US006991747B2

(12) United States Patent
Chiaradonna et al.

(10) Patent No.: US 6,991,747 B2
(45) Date of Patent: Jan. 31, 2006

(54) RADICAL SCAVENGER

(75) Inventors: Giuseppina Chiaradonna, Pisa (IT); Francesca Cicogna, Pisa (IT); Giovanni Ingrosso, Pisa (IT); Emanuela Franchi, Pisa (IT); Calogero Pinzino, Pisa (IT); Valerio Del Duca, Massalubrense (IT); Stefano Scialla, Roma (IT)

(73) Assignee: Procter & Gamble Company, Cincinnati, OH (US)

( * ) Notice: Subject to any disclaimer, the term of this patent is extended or adjusted under 35 U.S.C. 154(b) by 496 days.

(21) Appl. No.: 10/386,293

(22) Filed: Mar. 11, 2003

(65) Prior Publication Data

US 2004/0097391 A1    May 20, 2004

Related U.S. Application Data

(62) Division of application No. 10/110,911, filed as application No. PCT/US00/28795 on Oct. 18, 2000, now Pat. No. 6,569,826.

(30) Foreign Application Priority Data

Oct. 19, 1999   (EP)   ................ 998702187

(51) Int. Cl.
  *C07C 31/00*   (2006.01)
  *C07C 31/13*   (2006.01)
(52) U.S. Cl. .............. 252/186.38; 252/187.1; 560/8; 560/61; 426/250; 426/262; 44/600; 44/642; 514/1
(58) Field of Classification Search ........... 510/302, 510/378, 303, 379, 309, 380, 312, 505, 367, 510/370, 372, 376; 252/186.38, 187.1; 8/111, 8/137; 560/8, 61; 426/250, 262; 44/600, 44/642; 514/1
See application file for complete search history.

(56) References Cited

U.S. PATENT DOCUMENTS

| | | | |
|---|---|---|---|
| 1,985,424 A | 12/1934 | Piggott | |
| 2,082,275 A | 6/1937 | Daimler et al. | |
| 2,255,082 A | 9/1941 | Orthner et al. | |
| 2,702,279 A | 2/1955 | Funderburk et al. | |
| 2,703,798 A | 3/1955 | Schwartz | |
| 2,965,576 A | 12/1960 | Wilson | |
| 3,346,502 A | 10/1967 | Wixon | |
| 3,393,153 A | 7/1968 | Zimmerer et al. | |
| 3,646,015 A | 2/1972 | Hamilton | |
| 3,812,044 A | 5/1974 | Connor et al. | |
| 3,929,678 A | 12/1975 | Laughlin et al. | |
| 3,933,672 A | 1/1976 | Bartolotta et al. | |
| 4,021,365 A | 5/1977 | Sinka et al. | |
| 4,076,648 A | 2/1978 | Rosen | |
| 4,259,201 A | 3/1981 | Cockrell, Jr. et al. | |
| 4,623,476 A | 11/1986 | Nayer et al. | |
| 4,704,233 A | 11/1987 | Hartman et al. | |
| 4,749,740 A | 6/1988 | Aizawa et al. | |
| 4,790,856 A | 12/1988 | Wixon | |
| 4,818,425 A | 4/1989 | Meijer et al. | |
| 4,983,316 A | 1/1991 | Starch | |
| 5,035,825 A | 7/1991 | Eckhardt et al. | |
| 6,569,826 B1 | 5/2003 | Chiaradonna et al. | |

FOREIGN PATENT DOCUMENTS

| | | |
|---|---|---|
| EP | 062 523 B1 | 12/1987 |
| EP | 150 872 B2 | 4/1990 |
| EP | 206 718 B1 | 8/1990 |
| EP | 217 501 B1 | 7/1991 |
| EP | 186 386 B1 | 3/1992 |
| EP | 265 041 B1 | 11/1992 |
| EP | 322 564 B1 | 6/1994 |
| EP | 499 364 B1 | 10/1996 |
| EP | 573 699 B1 | 10/1996 |
| GB | 809060 | 2/1959 |
| GB | 1082179 | 9/1967 |
| GB | 1553610 | 10/1979 |
| GB | 1586769 | 3/1981 |
| GB | 2143231 A | 2/1985 |
| WO | WO 92/06070 A1 | 4/1992 |
| WO | WO 97/19054 A1 | 5/1997 |

OTHER PUBLICATIONS

D. A. Becker, *Highly Sensitive Colorimetric Detection and Facile Isolation of Diamagnetic Free Radical Adducts of Novel Chromotropic Nitrone Spin Trapping Agents Readily Derived from Guaiazulene*, J. Am. Chem. Soc., 1996, vol. 118, pp. 905-906.

S. Kurokawa et al., *Thermolysis of Pheny 3-Guaiazulenecarboxylate and the p-Acetyl and p-Methoxy Derivatives*, Bulletin of the Chemical Socity of Japan, 1976, vol. 49, No. 6, pp. 1650-1652.

*Primary Examiner*—Gregory R. Del Cotto
(74) *Attorney, Agent, or Firm*—James F. McBride; Kim W. Zerby; Steve W. Miller

(57) ABSTRACT

A new chromotropic compound, compositions containing such a compound and methods of using such compound, such as in a test method for identifying the presence of free radicals, are disclosed.

10 Claims, No Drawings

RADICAL SCAVENGER

CROSS REFERENCE TO RELATED APPLICATIONS

This application is a divisional of and claims priority under 35 U.S.C. § 120 to U.S. application Ser. No. 10/110,911 filed Apr. 17, 2002, now U.S. Pat. No. 6,569,286 which in turn is a U.S. National Stage entry under 35 U.S.C. § 371 of PCT International Application Serial No. PCT/US00/28795, filed Oct. 18, 2000, which claims priority to EP 99870218.7, filed Oct. 19, 1999.

TECHNICAL FIELD

The present invention relates to free radical scavenging compounds, compositions containing and test methods using such compounds.

BACKGROUND

Free radical scavenging compounds are those which bind, typically harmful free radicals that are generated as by-products of reactions. These compounds are generally known in the art. Examples of commonly used free radical scavengers include butyl hydroxy toluene (BHT), butyl hydroxyanisole (BHA), tertiary butyl hydroquinone (TBHQ), non-tert buty; hydroquinone (MTBHQ), ascorbic acid, propyl gallate.

Radical scavengers can be used in a number of applications to bind free radicals, for example in medicine as an antioxidant, in the preservation of fuels and foods and to stabilise bleaching compositions. By the term free radical it is meant fragments of molecules having one or more unpaired electrons for example .Cl, .OH, .ClO and carbon-centered free radicals like .CR(R')(R") and benzene derived free radicals. The Applicants have developed a new radical scavenging compound which provides at least parity, but more often improved binding of free radicals versus radical scavengers currently available in the art, for example butyl hyroxy toluene (BHT) and those other radical scavengers listed above.

Bleaching compositions comprising either an oxygen-releasing or a hypohalite-releasing bleaching agent can become unstable and loose bleaching power over time. This is possibly due to the reaction of the bleaching agent with heavy metal ions present as impurities in, for example raw materials or water. This reaction results in the decomposition of the bleaching agent and the release of free radicals. The free radicals present in bleaching compositions are intensely reactive and it is believed, further catalyse the decomposition of the bleaching agent. The Applicants have found that by inclusion of the free radical scavenger of the present invention in a bleaching composition, the stability of the composition over time is improved. In fact the radical scavenger of the present invention provide parity or improved radical scavenging versus for radical scavengers currently available in the art, for example butyl hyroxy toluene (BHT) and those other radical scavengers listed above in bleaching compositions.

Furthermore, free radicals are also believed to be detrimental to the integrity of the surface being bleached, for example a fabric. It is believed that the free radicals initiate a reaction of the fabric fibers themselves. An example of which is the oxidation of free hydroxide groups of cotton fibers contributing to the degradation and premature aging of the fabric. Fabric degradation and premature aging are most often identified by a loss of whiteness of the fabric. Hence it is a further advantage of the present invention that fabric whiteness can be maintained or improved by washing the fabric with compositions as described herein.

Further still, it has also been found that the radical scavenger compound of the present invention is a useful tool in detecting the presence of free radicals in any application not limited to cleaning compositions. Thus in a further aspect of the present invention is defined a test method for detecting free radicals by measuring the intensity of a colour change.

SUMMARY OF THE INVENTION

According to the present invention there is provided a chromophoric compound of the formula

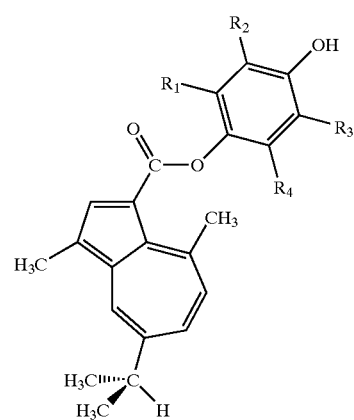

wherein the $R_1$ to $R_4$ groups can be either hydrogen, or methyl, or any alkyl or alkenyl or alkynyl group having from 1 to 20 carbon atoms.

In a further aspect of the present invention there is provided a cleaning composition comprising said compound. In yet a further aspect of the present invention there is provided a test method using said compound.

DETAILED DESCRIPTION OF THE INVENTION

The present invention relates to a chromophoric free radical scavenger having the general formula:

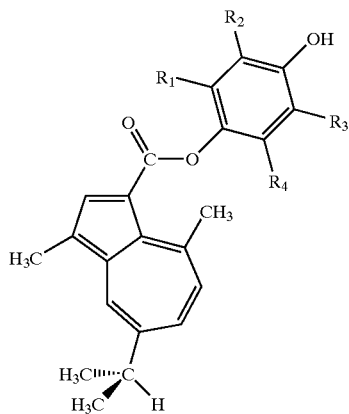

wherein the R1 to R4 groups can be either hydrogen, or methyl, or any alkyl or alkenyl or alkynyl group having from 1 to 20 carbon atoms.

The compounds of the present invention can be synthesised according to the general synthetic method described in the following diagram:

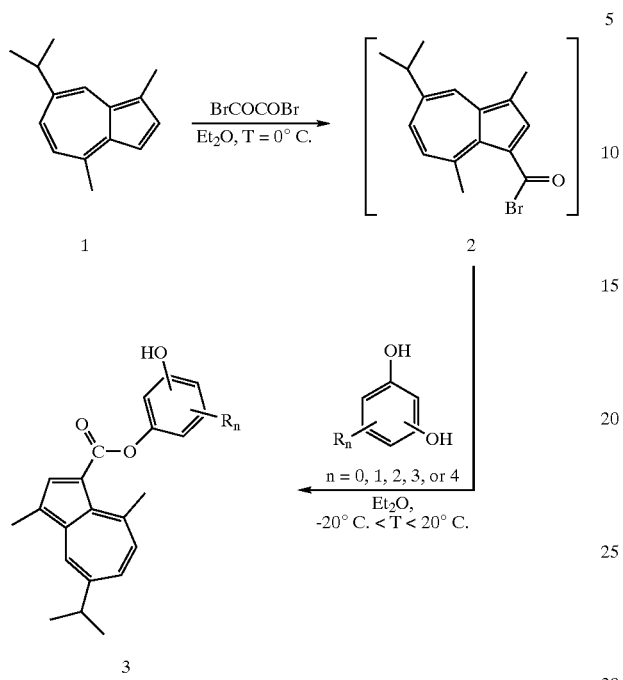

Guaiazaulene (1) and oxalyl bromide (2) are both commercially available products, as are most of the dihydroxybenzene derivatives.

Preferred synthesis routes for the radical scavenging compounds of the present invention are described in more detail in the following examples:

EXAMPLE 1

Preparation of 1,4-dimethyl-3-(4-hydroxylcarbophenoxy)-7-isopropylazulene

A solution of 0.5 ml of oxalyl bromide in 5 ml of diethyl ether (freshly distilled first from K/benzophenone and then from LiAlH$_4$) was added to a magnetically stirred solution of 0.5 g (2.5 mmol) of guaiazulene in 25 ml of diethyl ether, at 0° C., under a dry dinitrogen atmosphere. After 10 min, the mixture was allowed to warm to room temperature. After two hours, 70 ml of diethyl ether were added to the above reaction mixture which was then added dropwise to a solution of hydroquinone (0.55 g, 5 mmol) in diethyl ether (170 ml), at −10° C. The mixture was kept at room temperature for twelve hours. Then, it was treated with 30 ml of a 15% NaHCO$_3$ solution and with solid NaHCO$_3$ until neutral. The organic materials were extracted with benzene (3×30 ml). The combined extracts were dried over Na$_2$SO$_4$ and kept to dryness under reduced pressure (15–20 mmHg). A microcrystalline solid was so obtained which was dissolved in 20 ml of benzene. The resulting solution was subdivided into two 10 ml portions, and each of them was purified by column (length: 55 cm; internal diameter: 3 cm) chromatography on Silica gel 60 (Merck), using a 7/3 (v/v) diethyl ether/n-hexane mixture as eluant. The first band furnished unreacted guaiazulene. The title compound (0.34, 40% yield) was obtained as blue-violet solid from the third band.

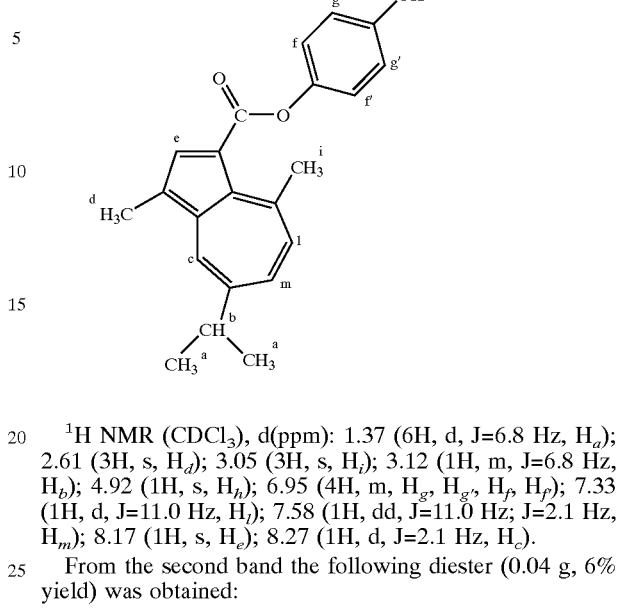

$^1$H NMR (CDCl$_3$), d(ppm): 1.37 (6H, d, J=6.8 Hz, H$_a$); 2.61 (3H, s, H$_d$); 3.05 (3H, s, H$_i$); 3.12 (1H, m, J=6.8 Hz, H$_b$); 4.92 (1H, s, H$_h$); 6.95 (4H, m, H$_g$, H$_{g'}$, H$_f$, H$_{f'}$); 7.33 (1H, d, J=11.0 Hz, H$_l$); 7.58 (1H, dd, J=11.0 Hz; J=2.1 Hz, H$_m$); 8.17 (1H, s, H$_e$); 8.27 (1H, d, J=2.1 Hz, H$_c$).

From the second band the following diester (0.04 g, 6% yield) was obtained:

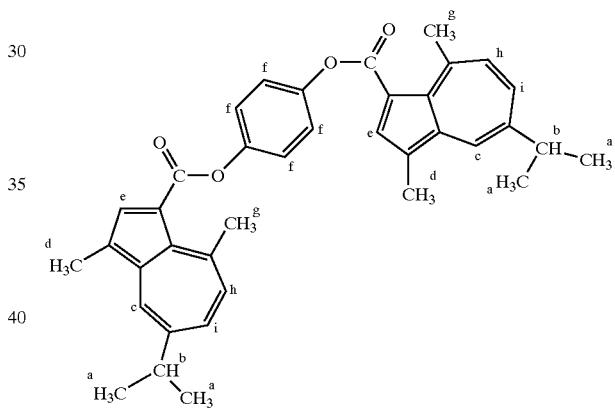

$^1$H NMR (CDCl$_3$), d(ppm): 1.37 (12H, d, H$_a$, J=6.8 Hz); 2.61 (6H, s, H$_d$); 3.05 (6H, s, H$_g$); 3.13 (2H, m, J=6.8 Hz, H$_b$); 7.30 (4H, s, H$_f$); 7.36 (2H, s, H$_h$); 7.57 (2H, dd, J=11.0 Hz; J=2.1 Hz, H$_i$); 8.19 (2H, s, H$_e$); 8.28 (2H, d, J=2.1 Hz, H$_c$).

EXAMPLE 2

Preparation of 1,4-dimethyl-3-(2,5-di-tert-butyl-4-hydroxyl-carbophenoxy)-7-isopropylazulene A solution of 0.5 ml of oxalyl bromide in 5 ml of diethyl ether (freshly distilled first from K/benzophenone and then from LiAlH$_4$) was added to a magnetically stirred solution of 0.5 g (2.5 mmol) of guaiazulene in 25 ml of diethyl ether, at 0° C., under a dry dinitrogen atmosphere. After 10 min, the mixture was allowed to warm to room temperature. After two hours, the mixture was transferred into a dropping funnel and added dropwise to a solution of 2,5-di-tert-butylhydroquinone (0.56 g, 2.5 mmol) in diethyl ether (25 ml), at 0° C. The reaction mixture was kept at room temperature for two hours. It was then treated with a 15% NaHCO$_3$ solution (ca. 30 ml) and with solid NaHCO$_3$ until neutral. The organic materials were extracted with benzene (3×30 ml). The combined extracts were dried over $Na_2SO_4$ and kept to dryness under reduced pressure (15–20 mmHg). A microcrystalline solid was so obtained which was dissolved in 6 ml of benzene. The resulting solution was purified by column (length: 45 cm; internal diameter: 3 cm) chromatography on Alumina 90 (Merck) (Activity grade, II-III; 70–230 mesh). The column was eluted first with n-hexane, which allowed to separate the unreacted guaiazulene, then with a 1/1 (v/v) n-hexane/diethyl ether mixture, which allowed to obtain the diester B as a microcrystalline solid (100 mg, 12%), and, finally with a 1/1 (v/v) ethyl acetate/diethyl ether, which allowed to obtain the title compound A as a microcrystalline blue solid (446 mg, 40% yield). The mass spectrum of A was obtained by EI technique and exhibited the molecular peak at m/z 446. The mass spectrum of B was obtained by IONSPRAY-MS, analyzing a methanolic solution of the sample: the pseudomolecular peaks at m/z 688 $[M+NH_4]^+$ and 671 $[M+H]^+$ were observed.

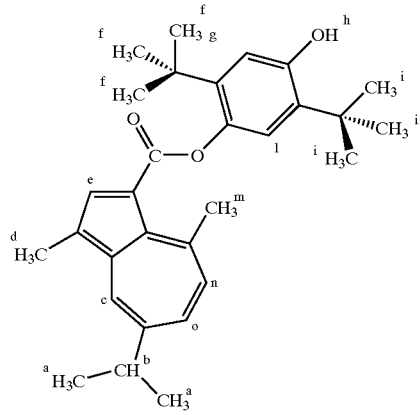

A $^1$H NMR of A, in $CDCl_3$, d(ppm): 1.30÷1.33 (24H, m, $H_a$, $H_f$, $H_i$); 2.56 (3H, s, $H_d$); 2.97 (3H, s, $H_m$); 3.08 (1H, m, J=6.8 Hz, $H_b$); 4.72 (1H, s, $H_h$); 6.63 (1H, s, $H_l$); 6.84 (1H, s, $H_g$); 7.25 (1H, d, J=11.0 Hz, $H_n$); 7.51 (1H, dd, J=11.0 Hz; J=2.1 Hz, $H_o$); 8.17 (1H, s, $H_e$); 8.23 (1H, d, J=2.1 Hz, $H_c$).

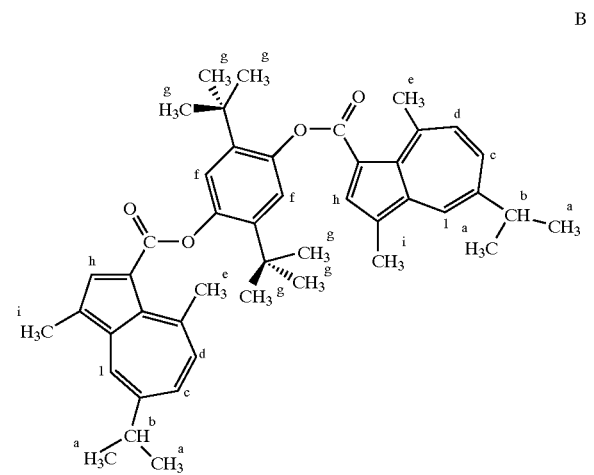

B $^1$H NMR of B, in $CDCl_3$, d(ppm): 1.42÷1.58 (30H, m, $H_a$, $H_g$); 2.73 (6H, s, $H_e$); 3.15 (6H, s, $H_e$); 3.22 (2H, m, J=6.8 Hz, $H_b$); 7.33 (2H, s, $H_f$); 7.42 (2H, d, J=11.0 Hz, $H_d$); 7.67 (2H, dd, J=11.0 Hz; J=2.1 Hz, $H_c$); 8.33 (2H, s, $H_h$); 8.39 (2H, d, J=2.1 Hz, $H_i$).

EXAMPLE 3

Preparation of 1,4-dimethyl-3-(2,3-dimethyl-4-hydroxyl-carbophenoxy)-7-isopropylazulene A solution of 0.5 ml of oxalyl bromide in 5 ml of diethyl ether (freshly distilled first from K/benzophenone and then from $LiAlH_4$) was added to a magnetically stirred solution of 0.5 g (2.5 mmol) of guaiazulene in 25 ml of diethyl ether, at 0° C., under a dry dinitrogen atmosphere. After 10 min, the mixture was allowed to warm to room temperature. After two hours, 70 ml of diethyl ether were added to the above reaction mixture which was then added dropwise to a solution of 2,3-dimethylhydroquinone (0.69 g, 5 mmol) in diethyl ether (170 ml), at −10° C. The mixture was kept at room temperature for twelve hours. Then it was treated with 30 ml of a 15% $NaHCO_3$ solution and with solid $NaHCO_3$ until neutral. The organic materials were extracted with benzene (3×30 ml). The combined extracts were dried over $Na_2SO_4$ and kept to dryness under reduced pressure (15–20 mmHg). A microcrystalline solid was so obtained which was dissolved in 15 ml of n-hexane. The resulting solution was purified by column (length: 30 cm; internal diameter: 3 cm) chromatography on Alumina 90 (Merck) (Activity grade, II-III; 70–230 mesh). The column was eluted first with n-hexane, which allowed to separate the unreacted guaiazulene, then with a 1/1 (v/v) $C_6H_6/CH_3COOEt$ mixture, which allowed to obtain the diester D as a microcystalline solid (160 mg, 22%), then with $C_6H_6$, wich allowed to separate the unreacted 2,3-dimethylhydroquinone and, finally, with HCOOEt, which allowed to obtain the title compound C as a microcystalline blue solid (362 mg, 27% yield).

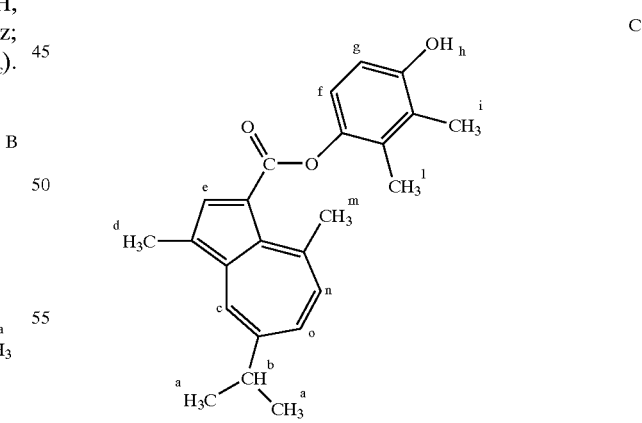

C $^1$H NMR of C, in $CDCl_3$, d(ppm): 1.37 (6H, d, J=6.8 Hz, $H_a$); 2.17 (3H, s, $H_i$); 2.18 (3H, s, $H_l$); 2.62 (3H, s, $H_d$); 3.10 (3H, s, $H_m$); 3.12 (1H, m, J=6.8 Hz, $H_b$); 4.69 (1H, s, $H_h$); 6.65 (1H, d, J=8.9 Hz, $H_g$); 6.95 (1H, d, J=8.9 Hz, $H_f$); 7.33 (1H, d, J=11.0 Hz, $H_n$); 7.57 (1H, dd, J=11.0 Hz; J=2.1 Hz, $H_o$); 8.23 (1H, s, $H_e$); 8.28 (1H, d, J=2.1 Hz, $H_c$).

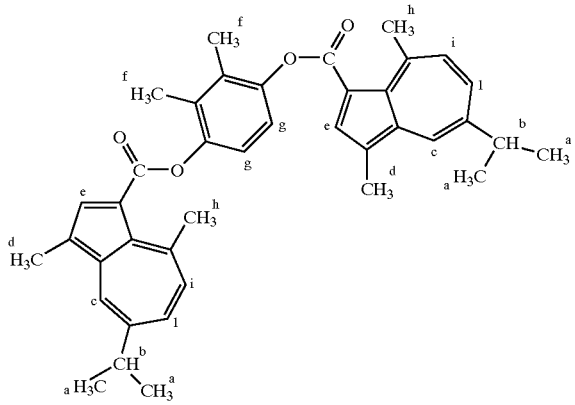

D

¹H NMR of D, in CDCl₃, d(ppm): 1.38 (12H, d, J=6.8 Hz, H$_a$); 2.24 (6H, s, H$_f$); 2.63 (6H, s, H$_d$); 3.06 (6H, s, H$_h$); 3.13 (2H, m, J=6.8 Hz, H$_b$); 7.10 (2H, s, H$_g$); 7.33 (2H, d, J=11.0 Hz, H$_l$); 7.58 (2H, dd, J=11.0 Hz; J=2.1 Hz, H$_i$); 8.23 (2H, s, H$_e$); 8.28 (1H, d, J=2.1 Hz, H$_c$).

EXAMPLE 4

Preparation of 1,4-dimethyl-3-(2-hydroxylcarbophenoxy)-7-isopropylazulene

A solution of 0.5 ml of oxalyl bromide in 5 ml of diethyl ether (freshly distilled first from K/benzophenone and then from LiAlH₄) was added to a magnetically stirred solution of 0.5 g (2.5 mmol) of guaiazulene in 25 ml of diethyl ether, at 0° C., under a dry dinitrogen atmosphere. After 10 min, the mixture was allowed to warm to room temperature. After two hours, 70 ml of diethyl ether were added to the above reaction mixture which was then added dropwise to a solution of catechol (0.55 g, 5 mmol) in diethyl ether (170 ml), at −15° C. The mixture was kept at room temperature for twelve hours. Then it was treated with 30 ml of a 15% NaHCO₃ solution and with solid NaHCO₃ until neutral. The organic materials were extracted with diethyl ether (3×30 ml). The combined extracts were dried over Na₂SO₄ and kept to dryness under reduced pressure (15–20 mmHg). A microcrystalline solid was so obtained which was dissolved in 10 ml of a benzene/ethyl acetate=9/1 (v/v) mixture. The resulting solution was purified by column (length: 50 cm; internal diameter: 3 cm) chromatography on Silica gel 60 (Merck)), using a 9/1 (v/v) benzene/ethyl acetate mixture as eluant. The title compound F (0.4 g, 48% yield) was obtained as blue-violet solid from the third band; while the second band furnished the diester G.

¹H NMR of F, in C₆D₆, d(ppm): 1.11 (6H, d, J=6.8 Hz, H$_a$); 2.35 (3H, s, H$_d$); 2.70 (1H, m, J=6.8 Hz, H$_b$); 3.05 (3H, s, H$_m$); 6.05 (1H, s, H$_l$); 6.7–7.3 (6H, m, H$_f$,H$_g$,H$_h$,H$_i$,H$_n$, H$_o$); 8.10 (1H, d, J=2.1 Hz, H$_c$); 8.23 (1H, s, H$_e$).

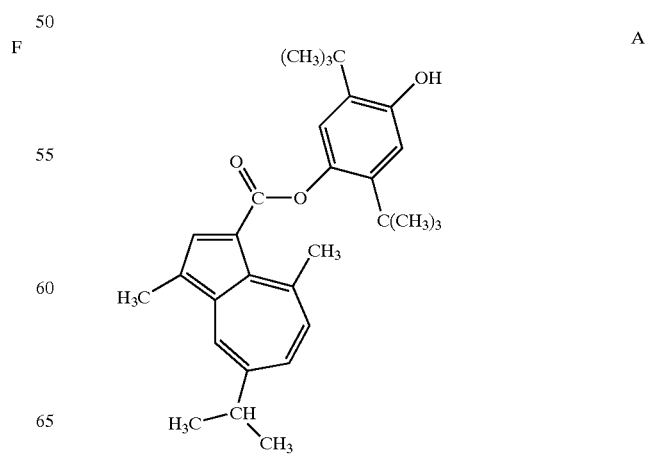

G

¹H NMR of G, in C₆D₆, d(ppm): 1.24 (12H, d, J=6.9 Hz, H$_a$); 2.54 (6H, s, H$_d$); 2.71 (6H, s, H$_h$); 2.95 (2H, m, J=6.9 Hz, H$_b$); 6.68 (4H, m, H$_f$, H$_g$); 6.90 (2H, d, J=11.0 Hz, H$_l$); 7.30 (2H, dd, J=11.0 Hz; J=2.1 Hz, H$_i$); 7.5 (2H, s, H$_e$); 8.08 (2H, d, J=2.1 Hz, H$_c$).

Test Method for Identifying Presence of Free Radicals

The compounds of the present invention are chromophoric meaning that the compounds described herein give the appearance of being coloured. Moreover the 'colour' of the compounds as seen by the viewer changes on reaction of the compound with free radicals. Thus the compounds as described herein may be used in the identification of the presence of free radicals. In fact the compounds of the present invention initially appear a violet/blue colour and then during reaction with free radicals, alter in form to appear a red to pale orange/yellow colour. Provided below are examples of the use of the compounds of the present invention in the identification of free radicals. These examples are however in no way meant to be limiting.

Reaction between the radical scavengers A, B and C with H₂O₂ in the presence of [Cu(en)₂][ClO₄]₂

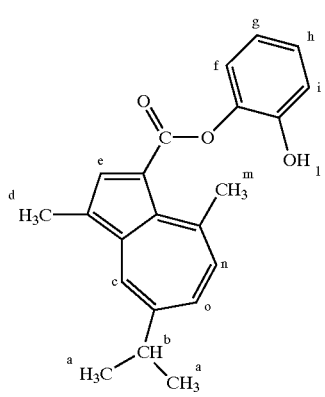

F

-continued

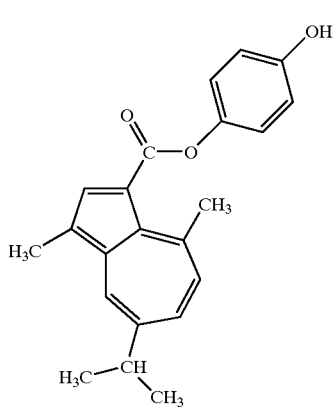

B

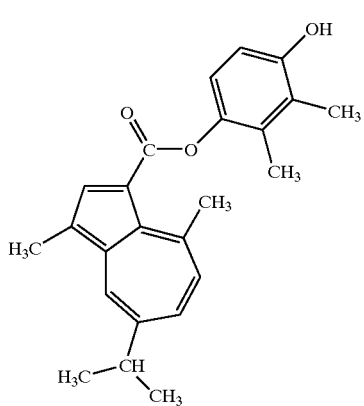

C 0.5 ml of a 2 M solution of $H_2O_2$ (pH 4) was introduced into a test-tube with 60 ml of a 0.012 M solution of A (or B or C) in NaAsC10 (C10 alkyl sulphate) and then reacted with 50 ml of a 0.01 M solution of $[Cu(en)_2][ClO_4]_2$ in water, at room temperature. In all cases, the blue-violet color of the mixture turned first red and then pale orange-yellow. The disappearance of the blue color was faster in the case of C than in the case of B and A. Anyway, in all cases the mixture became yellow in color within approximately 15 min. Afterwards, it was treated with 0.5 ml of ethyl formate and shaken for a few seconds. The organic layer was then tested by TLC on silica gel (eluant being benzene) in the case of the test carried out using A, on silica gel (eluant being ether/n-hexane=7/3, v/) when using B, and on alluminum oxide (eluant being ether/n-hexane=6/4, v/v) when using C. This allowed us to check the absence of unreacted A (or B or C) and the presence of three unidentified reaction products.

Reaction of the Radical Scavengers A, B, and C with $H_2O_2/[Cu(en)_2][ClO_4]_2$ in the Presence of BHT

TEST A: A/BHT=1/1

0.5 ml of a 2 M solution of $H_2O_2$ (pH 4) were introduced into a test-tube and then treated with 60 ml of a 0.012 M solution of A in NaAsC10 (product furnished by P&G RTC), 70 ml of a 0.01 M solution of BHT in NaAsC10 and, finally, with 50 ml of a 0.01 M solution of $[Cu(en)_2][ClO_4]_2$ in water, at room temperature. The mixture color did not turn red within ca. 25 seconds, as observed when operating in the absence of BHT, but only after 3 minutes. Within ca. 15 min the mixture became yellow in color and was then treated with 0.5 ml of ethyl formate and shaken for a few seconds. The organic layer was then tested by TLC on silica gel, using benzene as the eluant. This allowed us to check the presence of the unreacted A as well as of three unidentified products.

TEST B: A/BHT=1/2

This was carried out exactly as above, but using 30 ml of a 0.012 M solution of A in NaAsC10, i.e. operating at a A/BHT=1/2 molar ratio. The mixture color turned red only after ca. 5 min. Within ca. 15 min, the mixture became yellow in color. TLC analysis gave the same results as above.

TEST A: B/BHT=1/1

This was carried out exactly as reported for the Test A above. The mixture color did not turn red within ca. 20 seconds, as observed when operating in the absence of BHT, but only after 3 min. Within ca. 15 min, the mixture became yellow in color and was treated with 0.5 ml of ethyl formiate and shaken for a few seconds. The organic layer was then tested by TLC on silica gel, using an ether/n-hexane=7/3 (v/v) mixture as eluant. This allowed us to check the presence of the unreacted B as well as of three unidentified products.

TEST B: B/BHT=1/2

This was carried out exactly as reported for the Test B above, i.e. adopting a 1/2 B/BHT molar ratio. The mixture color turned red only after ca. 4 min and, within ca. 15 min, the mixture became yellow in color. TLC analysis gave the same results as above.

TEST A: C/BHT=1/1

This was carried out exactly as reported for the Tests A above. The mixture color did not turn red within ca. 10 seconds, as observed when operating in the absence of BHT, but only after 1 min. Within ca. 15 min, the mixture became yellow in color. Afterwards, the reaction mixture was treated with 0.5 ml of ethyl formiate and shaken for a few seconds. The organic layer was then tested by TLC on Alumina and the mixture ether/n-hexane=6/4 (v/v) as eluant. This allowed us to check the presence of the unreacted C as well as of three unidentified products.

TEST B: 5/BHT=1/2

This was carried out exactly as above, but operating at a 1/2 5/BHT molar ratio. The mixture color turned red only after ca. 2 min and, within ca. 15 min, the mixture became yellow in color. TLC analysis gave the same results as above.

Cleaning Compositions

The present invention also contemplates the free radical scavengers described above as components of a cleaning composition. The cleaning composition thus comprises as a first essential element thereof a chromotropic radical scavenging compound as described in more detail above.

The chromotropic compound is present in the cleaning composition at a level of from 0.001% to 10%, more preferably from 0.001% to 5% and most preferably from 0.001% to 1% by weight of the composition.

The cleaning compositions may be in solid or liquid form. By solid form it is meant particulates, for example powder or granular, tablets, blocks, briquettes and the like. By liquid form it is meant conventional liquid compositions and including gels and pastes.

The compositions of the present invention are preferably in liquid form. The liquid compositions herein are preferably aqueous compositions. The liquid compositions according to the present invention preferably have a pH up to 14, more preferably from 1 to 14, and even more preferably from 1.5 to 13.5.

Bleaching Agent

The composition according to the present invention comprise a bleaching agent as a second essential feature thereof.

The bleaching agent may be selected from any suitable bleaching agent currently available. In a preferred aspect the bleaching agent is selected from either peroxygen bleach and/or hypohalite bleach.

Suitable peroxygen bleaches to be used herein are hydrogen peroxide, water soluble sources thereof, or mixtures thereof. As used herein a hydrogen peroxide source refers to any compound which produces perhydroxyl ions when said compound is in contact with water.

Suitable water-soluble sources of hydrogen peroxide for use herein include percarbonates, persilicates, perborates, peroxyacids such as diperoxydodecandioic acid (DPDA) and pthaloylamido perhexanoic acid (PAP), magnesium perphtalic acid, perlauric acid, perbenzoic and alkylperbenzoic acids, hydroperoxides, aliphatic and aromatic diacyl peroxide's, and mixtures thereof. Preferred peroxygen bleaches herein are hydrogen peroxide, hydroperoxide and/or peroxyacids. Hydrogen peroxide is the most preferred peroxygen bleach herein.

Suitable hydroperoxides for use herein are tert-butyl hydroperoxide, cumyl hydroperoxide, 2,4,4-trimethylpentyl-2-hydroperoxide, di-isopropylbenzene-monohydroperoxide, tert-amyl hydroperoxide and 2,5-dimethyl-hexane-2,5-dihydroperoxide. Such hydroperoxides have the advantage to be particularly safe to fabrics and color while delivering excellent bleaching performance.

Suitable aliphatic diacyl peroxides for use herein are dilauroyl peroxide, didecanoyl peroxide, dimyristoyl peroxide, or mixtures thereof. Suitable aromatic diacyl peroxide for use herein is for example benzoyl peroxide. Such diacyl peroxides have the advantage to be particularly safe to fabrics and color while delivering excellent bleaching performance. Suitable aliphatic-aromatic diacyl peroxide for use herein is for example lauroyl benzoyl peroxide.

Hypohalite bleaches may be provided by a variety of sources, including bleaches that are oxidative bleaches and subsequently lead to the formation of positive halide ions as well as bleaches that are organic based sources of halides such as chloroisocyanurates.

Suitable hypohalite bleaches for use herein include the alkali metal and alkaline earth metal hypochlorites, hypobromites, hypoiodites, chlorinated trisodium phosphate dodecahydrates, potassium and sodium dichloroisocyanurates, potassium and sodium trichlorocyanurates, N-chloroimides, N-chloroamides, N-chloroamines and chlorohydantoins.

For the liquid compositions herein, the preferred hypohalite bleaches among the above described are the alkali metal and/or alkaline earth metal hypochlorites selected from the group consisting of sodium, potassium, magnesium, lithium and calcium hypochlorites, and mixtures thereof, more preferably the alkali metal sodium hypochlorite.

Typically, the compositions herein comprise from 0.1% to 20% by weight of the total composition of said peroxygen bleach or mixtures thereof, preferably from 1% to 15% and most preferably from 2% to 10%.

As mentioned above the compositions comprising the radical scavengers of the present invention are safe to fabrics and colour. Indeed loss of tensile strength or loss of colour intensity is reduced when using the compositions of the present invention as compared with similar bleaching compositions comprising either no radical scavenger or radical scavengers currently available in the art, for example BHT.

The tensile strength loss of a fabric may be measured by employing the Tensile Strength method. This method consists in measuring the tensile strength of a given fabric by stretching said fabric until it breakes. The force, expressed in Kg, necessary to break the fabric is the "Ultimate Tensile Stress" and may be measured with a Stress-Strain INSTRON® Machine available from INSTRON. The loss of tensile strength is the difference between the tensile strength of a fabric taken as a reference, i.e. a fabric which has not been bleached, and the tensile strength of the same fabric after having been bleached. A tensile strength loss of zero means that no fabric damage is observed.

Also fabric tensile strength loss reduction and/or color damage reduction are obtained according to the present invention, without compromising on the bleaching performance nor on the stain removal performance.

Optional Ingredients

The compositions herein may further comprise a variety of other optional ingredients such as pH buffering means, surfactants, chelating agents, brightener, further radical scavengers, antioxidants, builders, stabilisers, bleach activators, soil suspenders, soil suspending polyamine polymers, polymeric soil release agents, catalysts, dye transfer agents, solvents, brighteners, perfumes, pigments and dyes.

pH Buffering Means

The compositions of the present invention may include as an optional feature a pH buffering means or a mixture thereof. Where present the buffering means is preferably present at a level of from 0.1% to 10% by weight of the total composition. More preferably, the compositions herein comprise from 0.2% to 8% by weight of the total composition of a pH buffering means or a mixture thereof By "pH buffering means", it is meant herein any compound which when added to a solution makes the solution to resist to a change in hydrogen ion concentration on addition of acid or alkali.

A further advantage of the compositions of the present invention is that they are physically and chemically stable upon prolonged periods of storage. In fact, pH buffering means can be preferred optional ingredients of the present invention as they contribute to the excellent chemical stability of said compositions upon prolonged storage periods. More particularly a secondary benefit of the pH buffering means is that especially citric acid/citrate, used in the compositions herein act as antioxidants, i.e. they absorb oxygen present in the bleaching environment and thus reduce the oxidation decomposition of the oxidable ingredients present in the cleaning compositions, namely the peroxygen bleaches, perfumes, dyes and the like.

Chemical stability of the compositions herein may be evaluated by measuring the concentration of available oxygen (often abbreviated to AvO2) at given storage time after having manufactured the compositions. The concentration of available oxygen can be measured by chemical titration methods known in the art, such as the iodometric method, thiosulphatimetric method, the permanganometric method and the cerimetric method. Said methods and the criteria for the choice of the appropriate method are described for example in "Hydrogen Peroxide", W. C. Schumb, C. N. Satterfield and R. L. Wentworth, Reinhold Publishing Corporation, New York, 1955 and "Organic Peroxides", Daniel Swem, Editor Wiley Int. Science, 1970.

By "physically stable", it is meant herein that no phase separation occurs in the compositions for a period of 14 days at 50° C.

Surfactant

The compositions according to the present invention may comprise a surfactant or a mixture thereof as a highly preferred optional ingredient. Naturally, for the purpose of the present invention the surfactants are stable to the bleaching agent.

Typically, the compositions of the present invention comprise up to 60% by weight of the total composition of a surfactant or a mixture thereof, preferably from 0.1% to 30%, more preferably from 0.5% to 15% and most preferably from 1% to 10%.

Suitable surfactants for use herein include any nonionic, anionic, zwitterionic, cationic and/or amphoteric surfactants.

Particularly suitable surfactants for use herein are nonionic surfactants such as alkoxylated nonionic surfactants and/or polyhydroxy fatty acid amide surfactants and/or amine oxides and/or zwitterionic surfactants like the zwitterionic betaine surfactants described herein after.

Suitable alkoxylated nonionic surfactants for use herein are ethoxylated nonionic surfactants according to the formula RO—$(C_2H_4O)_nH$, wherein R is a $C_6$ to $C_{22}$ alkyl chain or a $C_6$ to $C_{28}$ alkyl benzene chain, and wherein n is from 0 to 20, preferably from 1 to 15 and, more preferably from 2 to 15 and most preferably from 2 to 12. The preferred R chains for use herein are the $C_8$ to $C_{22}$ alkyl chains. Propoxylated nonionic surfactants and ethoxy/propoxylated ones may also be used herein instead of the ethoxylated nonionic surfactants as defined herein above or together with said surfactants.

Preferred ethoxylated nonionic surfactants are according to the formula above and have an HLB (hydrophilic-lipophilic balance) below 16, preferably below 15, and more preferably below 14. Those ethoxylated nonionic surfactants have been found to provide good grease cutting properties.

Accordingly suitable ethoxylated nonionic surfactants for use herein are Dobanol® 91-2.5 (HLB=8.1; R is a mixture of C9 and $C_{11}$ alkyl chains, n is 2.5), or Lutensol® TO3 (HLB=8; R is a $C_{13}$ alkyl chains, n is 3), or Lutensol® AO3 (HLB=8; R is a mixture of $C_{13}$ and $C_{15}$ alkyl chains, n is 3), or Tergitol® 25L3 (HLB=7.7; R is in the range of $C_{12}$ to $C_{15}$ alkyl chain length, n is 3), or Dobanol® 23-3 (HLB=8.1; R is a mixture of $C_{12}$ and $C_{13}$ alkyl chains, n is 3), or Dobanol® 23-2 (HLB=6.2; R is a mixture of $C_{12}$ and $C_{13}$ alkyl chains, n is 2), or Dobanol® 45-7 (HLB=11.6; R is a mixture of $C_{14}$ and $C_{15}$ alkyl chains, n is 7) Dobanol® 23-6.5 (HLB=11.9; R is a mixture of $C_{12}$ and $C_{13}$ alkyl chains, n is 6.5), or Dobanol® 25-7 (HLB=12; R is a mixture of $C_{12}$ and $C_{15}$ alkyl chains, n is 7), or Dobanol® 91-5 (HLB=11.6; R is a mixture of $C_9$ and $C_{11}$ alkyl chains, n is 5), or Dobanol® 91-6 (HLB=12.5; R is a mixture of $C_9$ and $C_{11}$ alkyl chains, n is 6), or Dobanol® 91-8 (HLB=13.7; R is a mixture of $C_9$ and $C_{11}$ alkyl chains, n is 8), Dobanol® 91-10 (HLB=14.2; R is a mixture of $C_9$ to $C_{11}$ alkyl chains, n is 10), or mixtures thereof. Preferred herein are Dobanol® 91-2.5, or Lutensol® TO3, or Lutensol® AO3, or Tergitol® 25L3, or Dobanol® 23-3, or Dobanol® 23-2, or mixtures thereof. These Dobanol® surfactants are commercially available from SHELL. These Lutensol® surfactants are commercially available from BASF and these Tergitol® surfactants are commercially available from UNION CARBIDE.

Suitable chemical processes for preparing the alkoxylated nonionic surfactants for use herein include condensation of corresponding alcohols with alkylene oxide, in the desired proportions. Such processes are well-known to the man skilled in the art and have been extensively described in the art.

The compositions herein may desirably comprise one of those ethoxylated nonionic surfactants or a mixture of those ethoxylated nonionic surfactants having different HLBs (hydrophilic-lipophilic balance). In a preferred embodiment, the compositions herein comprise an ethoxylated nonionic surfactant according to the above formula and having an HLB up to 10 (i.e., a so called hydrophobic ethoxylated nonionic surfactant), preferably below 10, more preferably below 9, and an ethoxylated nonionic surfactant according to the above formula and having an HLB above 10 to 16 (i.e., a so called hydrophilic ethoxylated nonionic surfactant), preferably from 11 to 14. Indeed, in this preferred embodiment the compositions of the present invention typically comprise from 0.01% to 15% by weight of the total composition of said hydrophobic ethoxylated nonionic surfactant, preferably from 0.5% to 10% and from 0.01% to 15% by weight of said hydrophilic ethoxylated nonionic surfactant, preferably from 0.5% to 10%. Such mixtures of ethoxylated nonionic surfactants with different HLBs may be desired as they allow optimum grease cleaning removal performance on a broader range of greasy soils having different hydrophobic/hydrophilic characters.

Other particularly suitable nonionic surfactants for use herein include polyhydroxy fatty acid amide surfactants, or mixtures thereof, according to the formula:

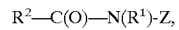

wherein $R^1$ is H, or $C_1$–$C_4$ alkyl, $C_1$–$C_4$ hydrocarbyl, 2-hydroxy ethyl, 2-hydroxy propyl or a mixture thereof, $R^2$ is $C_5$–$C_{31}$ hydrocarbyl, and Z is a polyhydroxyhydrocarbyl having a linear hydrocarbyl chain with at least 3 hydroxyls directly connected to the chain, or an alkoxylated derivative thereof.

Preferably, $R^1$ is $C_1$–$C_4$ alkyl, more preferably $C_1$ or $C_2$ alkyl and most preferably methyl, $R^2$ is a straight chain $C_7$–$C_{19}$ alkyl or alkenyl, preferably a straight chain $C_9$–$C_{18}$ alkyl or alkenyl, more preferably a straight chain $C_{11}$–$C_{18}$ alkyl or alkenyl, and most preferably a straight chain $C_{11}$–$C_{14}$ alkyl or alkenyl, or mixtures thereof. Z preferably will be derived from a reducing sugar in a reductive amination reaction; more preferably Z is a glycityl. Suitable reducing sugars include glucose, fructose, maltose, lactose, galactose, mannose and xylose. As raw materials, high dextrose corn syrup, high fructose corn syrup, and high maltose corn syrup can be utilised as well as the individual sugars listed above. These corn syrups may yield a mix of sugar components for Z. It should be understood that H is by no means intended to exclude other suitable raw materials. Z preferably will be selected from the group consisting of —$CH_2$—$(CHOH)_n$—$CH_2OH$, —$CH(CH_2OH)$—$(CHOH)_{n-1}$—$CH_2OH$, —$CH_2$—$(CHOH)_2$—$(CHOR')(CHOH)$—$CH_2OH$, where n is an integer from 3 to 5, inclusive, and R' is H or a cyclic or aliphatic monosaccharide, and alkoxylated derivatives thereof. Most preferred are glycityls wherein n is 4, particularly $CH_2$—$(CHOH)_4$—$CH_2OH$.

In formula $R^2$—C(O)—N($R^1$)-Z, $R^1$ can be, for example, N-methyl, N-ethyl, N-propyl, N-isopropyl, N-butyl, N-2-hydroxy ethyl, or N-2-hydroxy propyl. $R^2$—C(O)—N< can be, for example, cocamide, stearamide, oleamide, lauramide, myristamide, capricamide, palmitamide, tallowamide and the like. Z can be 1-deoxyglucityl, 2-deoxyfructityl, 1-deoxymaltityl, 1-deoxylactityl, 1-deoxygalactityl, 1-deoxymannityl, 1-deoxymaltotriotityl and the like.

Suitable polyhydroxy fatty acid amide surfactants to be used herein may be commercially available under the trade name HOE® from Hoechst.

Methods for making polyhydroxy fatty acid amide surfactants are known in the art. In general, they can be made by reacting an alkyl amine with a reducing sugar in a reductive amination reaction to form a corresponding N-alkyl polyhydroxyamine, and then reacting the N-alkyl polyhydroxyamine with a fatty aliphatic ester or triglyceride in a condensationlamidation step to form the N-alkyl, N-polyhydroxy fatty acid amide product. Processes for making compositions containing polyhydroxy fatty acid amides are disclosed for example in GB patent specification 809,060, published Feb. 18, 1959, by Thomas Hedley & Co., Ltd., U.S. Pat. No. 2,965,576, issued Dec. 20, 1960 to E. R. Wilson, U.S. Pat. No. 2,703,798, Anthony M. Schwartz, issued Mar. 8, 1955, U.S. Pat. No. 1,985,424, issued Dec. 25, 1934 to Piggott and WO92/06070, each of which is incorporated herein by reference.

Other suitable nonionic surfactants for use herein include amine oxides having the following formula $R_1R_2R_3NO$ wherein each of R1, R2 and R3 is independently a saturated substituted or unsubstituted, linear or branched hydrocarbon chain of from 1 to 30 carbon atoms. Preferred amine oxide surfactants to be used according to the present invention are amine oxides having the following formula $R_1R_2R_3NO$ wherein R1 is an hydrocarbon chain comprising from 1 to 30 carbon atoms, preferably from 6 to 20, more preferably from 8 to 16, most preferably from 8 to 12, and wherein R2 and R3 are independently substituted or unsubstituted, linear or branched hydrocarbon chains comprising from 1 to 4 carbon atoms, preferably from 1 to 3 carbon atoms, and more preferably are methyl groups. R1 may be a saturated substituted or unsubstituted linear or branched hydrocarbon chain. Suitable amine oxides for use herein are for instance natural blend C8–C10 amine oxides as well as C12–C16 amine oxides commercially available from Hoechst.

Another class of surfactants particularly suitable for use herein include zwitterionic betaine surfactants containing both a cationic hydrophilic group, i.e., a quaternary ammonium group, and anionic hydrophilic group on the same molecule at a relatively wide range of pH's. The typical anionic hydrophilic groups are carboxylates and sulfonates, although other groups like sulfates, phosphonates, and the like can be used. A generic formula for the zwitterionic betaine surfactants for use herein is:

$$R_1-N^+(R_2)(R_3)R_4X-$$

wherein $R_1$ is a hydrophobic group; $R_2$ is hydrogen, $C_1-C_6$ alkyl, hydroxy alkyl or other substituted $C_1-C_6$ alkyl group; $R_3$ is $C_1-C_6$ alkyl, hydroxy alkyl or other substituted $C_1-C_6$ alkyl group which can also be joined to $R_2$ to form ring structures with the N, or a $C_1-C_6$ carboxylic acid group or a $C_1-C_6$ sulfonate group; $R_4$ is a moiety joining the cationic nitrogen atom to the hydrophilic group and is typically an alkylene, hydroxy alkylene, or polyalkoxy group containing from 1 to 10 carbon atoms; and X is the hydrophilic group which is a carboxylate or sulfonate group.

Preferred hydrophobic groups $R_1$ are aliphatic or aromatic, saturated or unsaturated, substituted or unsubstituted hydrocarbon chains that can contain linking groups such as amido groups, ester groups. More preferred $R_1$ is an alkyl group containing from 1 to 24 carbon atoms, preferably from 8 to 18, and more preferably from 10 to 16. These simple alkyl groups are preferred for cost and stability reasons. However, the hydrophobic group $R_1$ can also be an amido radical of the formula $R_a-C(O)-NH-(C(R_b)_2)_m$, wherein $R_a$ is an aliphatic or aromatic, saturated or unsaturated, substituted or unsubstituted hydrocarbon chain, preferably an alkyl group containing from 8 up to 20 carbon atoms, preferably up to 18, more preferably up to 16, 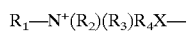 is selected from the group consisting of hydrogen and hydroxy groups, and m is from 1 to 4, preferably from 2 to 3, more preferably 3, with no more than one hydroxy group in any $(C(R_b)_2)$ moiety.

Preferred $R_2$ is hydrogen, or a $C_1-C_3$ alkyl and more preferably methyl. Preferred $R_3$ is a $C_1-C_4$ carboxylic acid group or C1–C4 sulfonate group, or a $C_1-C_3$ alkyl and more preferably methyl. Preferred $R_4$ is $(CH2)_n$ wherein n is an integer from 1 to 10, preferably from 1 to 6, more preferably is from 1 to 3.

Some common examples of betaine/sulphobetaine are described in U.S. Pat. Nos. 2,082,275, 2,702,279 and 2,255,082, incorporated herein by reference.

Examples of particularly suitable alkyldimethyl betaines include coconut-dimethyl betaine, lauryl dimethyl betaine, decyl dimethyl betaine, 2-(N-decyl-N, N-dimethyl-ammonia)acetate, 2-(N-coco N, N-dimethylammonio) acetate, myristyl dimethyl betaine, palmityl dimethyl betaine, cetyl dimethyl betaine, stearyl dimethyl betaine. For example Coconut dimethyl betaine is commercially available from Seppic under the trade name of Amonyl 265®. Lauryl betaine is commercially available from Albright & Wilson under the trade name Empigen BB/L®.

Examples of amidobetaines include cocoamidoethylbetaine, cocoamidopropyl betaine or C10–C14 fatty acylamidopropylene(hydropropylene)sulfobetaine. For example C10–C14 fatty acylamidopropylene(hydropropylene)sulfobetaine is commercially available from Sherex Company under the trade name "Varion CAS® sulfobetaine".

A further example of betaine is Lauryl-immino-dipropionate commercially available from Rhone-Poulenc under the trade name Mirataine H2C-HA®.

Particularly preferred zwitterionic betaine surfactants for use herein are salt free, i.e. that the zwitterionic betaine surfactant raw material contains less than 5% by weight of salts, preferably less than 2%, more preferably less than 1% and most preferably from 0.01% to 0.5%.

By "salts" is meant herein any material having as base unit, a couple of positive ion (or positive molecular ion) and negative ion (or negative molecular ion) containing one or more halogen atoms. Such salts include Sodium Chloride, Potassium Chloride, Sodium Bromide and the like.

Such salts free zwitterionic betaine surfactants are obtainable by conventional manufacturing processes like inverse osmosis or fractionated precipitation. For example inverse osmosis is based on the principle of contacting the zwitterionic betaine surfactant raw material (commercially available) with a polar solvent (it is to be understood that such a solvent is free of salts) separated by a semi-permeable membrane for example acetate-cellulose. An adequate pressure is applied on the system to allow the salts to migrate from the surfactant raw material to the polar solvent phase. This way the zwitterionic betaine surfactant raw material is purified, i.e. the salts is subtracted from the raw material.

Advantageously, it has now been surprisingly found that the use of such salt free zwitterionic betaine surfactants deliver improved fabric safety and/or color safety when bleaching fabrics with a peroxygen bleach-containing composition comprising the same, as compared to the use of the same zwitterionic betaine surfactants with higher amount of salts. Thus, in its broadest aspect, the present invention also encompasses the use of a composition comprising a salt free zwitterionic betaine surfactant, a peroxygen bleach and a pH buffering means for bleaching soiled fabrics, especially pretreating soiled fabrics, whereby color safety is improved (i.e. color damage/decoloration is reduced) and/or fabric safety is improved.

In a preferred embodiment, herein the surfactants present in the compositions of the present invention are a mixture of ethoxylated nonionic surfactants and betaine zwitterionic surfactants. Indeed, such betaine zwitterionic surfactants and ethoxylated nonionic surfactants act together to deliver excellent stain removal on greasy stains (e.g., lipstick, olive oil, mayonnaise, vegetal oil, sebum, make-up), while providing improved bleaching performance to the liquid peroxygen bleach-containing compositions of the present invention comprising them.

Indeed, a significant co-operation has been observed between these ingredients to get optimum stain removal performance on a variety of soils, from particulate to non-particulate soils from hydrophobic to hydrophilic soils under any household application and especially laundry application on both hydrophilic and hydrophobic fabrics.

Optimum stain removal performance and bleaching performance are obtained when the ethoxylated nonionic surfactant and the zwitterionic betaine surfactant are present in the compositions of the present invention comprising a peroxygen bleach (pH below 7), at weight ratio of the ethoxylated nonionic surfactant to the zwitterionic betaine surfactant of from 0.01 to 20, preferably from 0.1 to 15, more preferably from 0.5 to 5 and most preferably from 0.6 to 3.

Importantly, the improved stain removal benefit and bleaching benefit are delivered with a liquid composition which is a water-like, clear and transparent composition. The appearance of a composition can be evaluated via turbidimetric analysis. For example, the transparency of a composition can be evaluated by measuring its absorbency via a spectrophotometer at 800 nm wave length.

Although less desirable than the surfactants mentioned above for their stain removal properties, other surfactants may be used in the compositions herein. Suitable anionic surfactants for use in the compositions herein include water-soluble salts or acids of the formula $ROSO_3M$ wherein R preferably is a $C_{10}$–$C_{24}$ hydrocarbyl, preferably an alkyl or hydroxyalkyl having a $C_{10}$–$C_{20}$ alkyl component, more preferably a $C_{12}$–$C_{18}$ alkyl or hydroxyalkyl, and M is H or a cation, e.g., an alkali metal cation (e.g., sodium, potassium, lithium), or ammonium or substituted ammonium (e.g., methyl-, dimethyl-, and trimethyl ammonium cations and quaternary ammonium cations, such as tetramethyl-ammonium and dimethyl piperdinium cations and quaternary ammonium cations derived from alkylamines such as ethylamine, diethylamine, triethylamine, and mixtures thereof, and the like). Typically, alkyl chains of $C_{12-16}$ are preferred for lower wash temperatures (e.g., below about 50° C.) and $C_{16-18}$ alkyl chains are preferred for higher wash temperatures (e.g., above about 50° C.).

Other suitable anionic surfactants for use herein are water-soluble salts or acids of the formula $RO(A)_mSO_3M$ wherein R is an unsubstituted $C_{10}$–$C_{24}$ alkyl or hydroxyalkyl group having a $C_{10}$–$C_{24}$ alkyl component, preferably a $C_{12}$–$C_{20}$ alkyl or hydroxyalkyl, more preferably $C_{12}$–$C_{18}$ alkyl or hydroxyalkyl, A is an ethoxy or propoxy unit, m is greater than zero, typically between about 0.5 and about 6, more preferably between about 0.5 and about 3, and M is H or a cation which can be, for example, a metal cation (e.g., sodium, potassium, lithium, calcium, magnesium, etc.), ammonium or substituted-ammonium cation. Alkyl ethoxylated sulfates as well as alkyl propoxylated sulfates are contemplated herein. Specific examples of substituted ammonium cations include methyl-, dimethyl-, trimethyl-ammonium and quaternary ammonium cations, such as tetramethyl-ammonium, dimethyl piperdinium and cations derived from alkanolamines such as ethylamine, diethylamine, triethylamine, mixtures thereof, and the like. Exemplary surfactants are $C_{12}$–$C_{18}$ alkyl polyethoxylate (1.0) sulfate, $C_{12}$–$C_{18}E(1.0)M$, $C_{12}$–$C_{18}$ alkyl polyethoxylate (2.25) sulfate, $C_{12}$–$C_{18}E(2.25)M$), $C_{12}$–$C_{18}$ alkyl polyethoxylate (3.0) sulfate, C12–C15 alkyl ethoxylate (3) sulphate, $C_{12}$–$C_{18}$ alkyl polyethoxylate (4.0) sulfate, $C_{12}$–$C_{18}E$ (4.0)M, wherein M is conveniently selected from sodium and potassium.

Other anionic surfactants useful for detersive purposes can also be used herein. These can include salts (including, for example, sodium, potassium, ammonium, and substituted ammonium salts such as mono-, di- and triethanolamine salts) of soap, $C_9$–$C_{20}$ linear alkylbenzenesulfonates, $C_8$–$C_{22}$ primary or secondary alkanesulfonates, $C_8$–$C_{24}$ olefinsulfonates, sulfonated polycarboxylic acids prepared by sulfonation of the pyrolyzed product of alkaline earth metal citrates, e.g., as described in British patent specification No. 1,082,179, $C_8$–$C_{24}$ alkylpolyglycolethersulfates (containing up to 10 moles of ethylene oxide); alkyl ester sulfonates such as $C_{14-16}$ methyl ester sulfonates; acyl glycerol sulfonates, fatty oleyl glycerol sulfates, alkyl phenol ethylene oxide ether sulfates, paraffin sulfonates, alkyl phosphates, isethionates such as the acyl isethionates, N-acyl taurates, alkyl succinamates and sulfosuccinates, monoesters of sulfosuccinate (especially saturated and unsaturated $C_{12}$–$C_{18}$ monoesters) diesters of sulfosuccinate (especially saturated and unsaturated $C_6$–$C_{14}$ diesters), sulfates of alkylpolysaccharides such as the sulfates of alkylpolyglucoside (the nonionic nonsulfated compounds being described below), branched primary alkyl sulfates, alkyl polyethoxy carboxylates such as those of the formula $RO(CH_2CH_2O)_kCH_2COO-M^+$ wherein R is a $C_8$–$C_{22}$ alkyl, k is an integer from 0 to 10, and M is a soluble salt-forming cation. Resin acids and hydrogenated resin acids are also suitable, such as rosin, hydrogenated rosin, and resin acids and hydrogenated resin acids present in or derived from tall oil. Further examples are given in "Surface Active Agents and Detergents" (Vol. I and II by Schwartz, Perry and Berch). A variety of such surfactants are also generally disclosed in U.S. Pat. No. 3,929,678, issued Dec. 30, 1975, to Laughlin, et al. at Column 23, line 58 through Column 29, line 23 (herein incorporated by reference).

Other suitable anionic surfactants for use herein also include acyl sarcosinate or mixtures thereof, in its acid and/or salt form, preferably long chain acyl sarcosinates having the following formula:

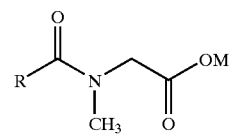

wherein M is hydrogen or a cationic moiety and wherein R is an alkyl group of from 11 to 15 carbon atoms, preferably of from 11 to 13 carbon atoms. Preferred M are hydrogen and alkali metal salts, especially sodium and potassium. Said acyl sarcosinate surfactants are derived from natural fatty acids and the amino-acid sarcosine (N-methyl glycine). They are suitable to be used as aqueous solution of their salt or in their acidic form as powder. Being derivatives of natural fatty acids, said acyl sarcosinates are rapidly and completely biodegradable and have good skin compatibility.

Accordingly, suitable long chain acyl sarcosinates for use herein include $C_{12}$ acyl sarcosinate (i.e., an acyl sarcosinate according to the above formula wherein M is hydrogen and R is an alkyl group of 11 carbon atoms) and $C_{14}$ acyl sarcosinate (i.e., an acyl sarcosinate according to the above formula wherein M is hydrogen and R is an alkyl group of 13 carbon atoms). $C_{12}$ acyl sarcosinate is commercially available, for example, as Hamposyl L-30® supplied by Hampshire. $C_{14}$ acyl sarcosinate is commercially available, for example, as Hamposyl M-30® supplied by Hampshire.

Brightener

A preferred optional component of the invention is a brightener. Any brightener known in the art may be used herein including both hydrophobic and hydrophilic brighteners and mixtures thereof.

Brighteners are compounds which have the ability to fluoresce by absorbing ultraviolet wave-lengths of light and re-emitting visible light. Brighteners, also referred to as fluorescent whitening agents (FWA), have been extensively described in the art, see for instance EP-A-0 265 041, EP-A-0 322 564, EP-A-0 317 979 or "Fluorescent whitening agents" by A. K. Sarkar, published by MERROW, especially page 71–72.

Commercial optical brighteners which may be useful in the present invention can be classified into subgroups, which include, but are not necessarily limited to, derivatives of stilbene, pyrazoline, coumarin, carboxylic acid, methinecyanine, dibenzothiophene-5,5-dioxide, azole, 5- and 6-membered-ring heterocycle, and other miscellaneous agents. Examples of such brighteners are disclosed in "The Production and Application of Fluorescent Brightening Agents", M. Zahradnik, Published by John Wiley & Sons, New York (1982). Further optical brighteners which may also be used in the present invention include naphthlimide, benzoxazole, benzofuran, benzimidazole and any mixtures thereof. Particularly preferred brighteners for use herein are the derivatives of stilbene and mixtures thereof.

Examples of optical brighteners which are useful in the present compositions are those identified in U.S. Pat. No. 4,790,856. These brighteners include the PHORWHITE® series of brighteners from Verona. Other brighteners disclosed in this reference include: Tinopal-UNPA®, Tinopal CBS® and Tinopal 5BM® available from Ciba-Geigy; Artic White CC® and Artic White CWD®; the 2-(4-styryl-phenyl)-2H-naptho[1,2-d]triazoles; 4,4'-bis(1,2,3-triazol-2-yl)-stilbenes; 4,4'-bis(styryl)bisphenyls; and the aminocoumarins.

Specific examples of brighteners useful herein include 4-methyl-7-diethyl-amino coumarin; 1,2-bis(-benzimidazol-2-yl)ethylene; 1,3-diphenyl-pyrazolines; 2,5-bis(benzoxazol-2-yl)thiophene; 2-styryl-naptho-[1,2-d]oxazole; 2-(stilbene-4-yl)-2H-naphtho[1,2-d]triazole, 3-phenyl-7-(isoindolinyl) coumarin; 3-methyl-7-(isoindolinyl) coumarin; 3-chloro-7-(isoindolinyl) coumarin; 4-(isoindolinyl)-4'-methylstilbene; 4-(isoindolinyl)-4'-methoxystilbene; sodium 4-(isoindolinyl)-4'-stilbenesulfonate; 4-(isoindolinyl)-4'-phenylstilbene; 4-(isoindolinyl)-3-methoxy-4'-methylstilbene; 4-(2-chloroisoindolinyl)-4'-(2-methylisoindolinyl)-2,2'-stilbenedisosulfonic acid; disodium 4,4'-diisoindolinyl-2,2'-stilbene disulfonate; 4,4'-diisoindolinyl-2,2'-stilbenedisulfonamide; disodium 4,4'-(7,8-dichloro-1-isoindolinyl)2,2-stilbenedisulfonate; disodium 4,4'-(7-chloro-1-isoindolinyl)2,2-stilbenedisulfonate; disodium 4,4'-(6-lsopropoxy-1-isoindolinyl)2,2-stilbenedisulfonate; disodium 4,4'-(7,8-diisopropyl-1-isoindolinyl)2,2-stilbene-disulfonate; disodium 4,4'-(7-butoxy-1-isoindolinyl)2,2-stilbenedisulfonate; disodium 4,4'-(6-trifluoromethyl-1-isoindolinyl)2,2-stilbenedisulfonate; disodium 4,4'-[6-(1,4,7-trioxanonyl)-1-isoindolinyl)]2,2-stilbenedisulfonate; disodium 4,4'-(7-methoxymethyl-1-isoindolinyl)2,2-stilbenedisulfonate; disodium 4,4'-(6-phenyl-1-isoindolinyl)2,2-stilbenedisulfonate; disodium 4,4'-(6-naphthyl-1-isoindolinyl)2,2-stilbenedisulfonate; disodium 4,4'-(6-methylsulfonyl-1-isoindolinyl)2,2-stilbenedisulfonate; disodium 4,4'-(7-cyano-1-isoindolinyl)2,2-stilbenedisulfonate; and disodium 4,4'-[7-(1,2,3-trihydroxypropyl)-1-isoindolinyl)]2,2-stilbenedisulfonate; disodium 4-isoindolinyl-4'-ethoxy-2,2'-stilbenedisulfonate; disodium 4-isoindolinyl-4'-methoxy-2,2'-stilbenedisulfonate; disodium 4-isoindolinyl-4'-ethoxy-2,2'-stilbenedisulfonamide; disodium 4-isoindolinyl-4'-methyl-2,2'-stilbenedisulfonamide; disodium 4,4'-bis-(2-diethanolamino-4-anilino-s-triazin-6-ylamino)stilbene-2:2 disulphonate, disodium 4,4'-bis-(2-morpholino-4-anilino-s-triazin-6-ylamino)-stilbene-2:2'-disulphonate, disodium 4,4'-bis-(2,4-dianilino-s-triazin-6-ylamino)-stilbene-2-sulphonate, monosodium 4,4"-bis-(2,4-dianilino-s-triazin-6-ylamino)-stilbene-2:2'-disulphonate, disodium 4,4'-bis-(2-anilino-4-(N-methyl-N-2-hydroxyethylamino)-s-triazin-6-ylamino)stilbene-2,2'-disulphonate, disodium 4,4'-bis-(4-phenyl-2,1,3-triazol-2-yl)-stilbene-2,2' disulphonate, disodium 4,4'-bis-(2-anilino-4-(1-methyl-2-hydroxyethylamino)-s-triazin-6-ylamino)-stilbene-2,2'-disulphonate, sodium 2-(stilbyl-4"-(naphtho-1',2':4,5)-1,2,3-triazole-2"-sulphonate, 4,4'-bis-(2-sulphostyryl)-biphenyl, 4,4'-bis(4-phenyl-2H-1,2,3-triazol-2-yl)-2,2'-stilbenedisulfonic acid and mixture thereof. See also U.S. Pat. No. 3,646,015, U.S. Pat. No. 3,346,502 and U.S. Pat. No. 3,393,153 for further examples of brighteners useful herein.

Indeed one of the functionally equivalent derivative salts of 4,4'-bis(4-phenyl-2H-1,2,3-triazol-2-yl)-2,2'-stilbenedisulfonic acid, namely its sodium salt is available from Mobay Chemical Corporation, a subsidiary of Bayer AG under the name Phorwite® CAN. The amine salt is available from Molay under the name Phorwite® CL solution. The potassium salt is available under the name Phorwite® BHC 766.

Specific examples of hydrophilic optical brighteners useful in the present invention are those having the structural formula:

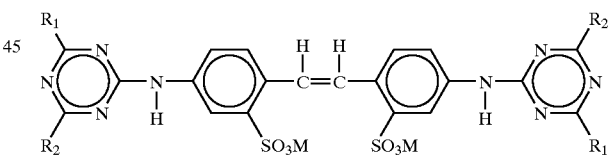

wherein $R_1$ is selected from anilino, N-2-bis-hydroxyethyl and NH-2-hydroxyethyl; $R_2$ is selected from N-2-bis-hydroxyethyl, N-2-hydroxyethyl-N-methylamino, morphilino, chloro and amino; and M is a salt-forming cation such as sodium or potassium.

When in the above formula, $R_1$ is anilino, $R_2$ is N-2-bis-hydroxyethyl and M is a cation such as sodium, the brightener is 4,4',-bis[(4-anilino-6-(N-2-bis-hydroxyethyl)-s-triazine-2-yl)amino]-2,2'-stilbenedisulfonic acid and disodium salt. This particular brightener species is commercially marketed under the tradename Tinopal-UNPA-GX by Ciba-Geigy Corporation. Tinopal-UNPA-GX is the preferred hydrophilic optical brightener useful in the detergent compositions herein.

When in the above formula, $R_1$ is anilino, $R_2$ is N-2-hydroxyethyl-N-2-methylamino and M is a cation such as sodium, the brightener is 4,4'-bis[(4-anilino-6-(N-2-hydroxyethyl-N-methylamino)-s-triazine-2-yl)amino]2,2'-stilbenedisulfonic acid disodium salt. This particular brightener species is commercially marketed under the tradename Tinopal 5BM-GX by Ciba-Geigy Corporation.

When in the above formula, $R_1$ is anilino, $R_2$ is morpholino and M is a cation such as sodium, the brightener is 4,4'-bis[(4-anilino-6-morpholino-s-triazine-2-ylamino]2,2'-stilbenedisulfonic acid, sodium salt. This particular brightener species is commercially marketed under the tradename Tinopal AMS-GX by Ciba Geigy Corporation.

Another preferred brightener is Optiblanc BRB available from 3V sigma.

Other substituted stilbene 2,2'-disulfonic acid derivatives also include 4-4'-bis (2-2' styryl sulfonate) biphenyl, commercially available from Ciba-Geigy under the trade name Brightener 49® or other hydrophilic brighteners like for example Brightener 3® or Brightener 47®, also commercially available from Ciba-Geigy.

Specific examples of hydrophobic brighteners useful in the present invention include the polycyclic oxazole derivatives such as benzo-oxazole derivatives, or mixtures thereof and particularly preferred herein the benzo-oxazole derivatives. An example of such a brightener is benzoxazole,2,2'-(thiophenaldyl)bis having the following formula C18H10N2O2S, commercially available from Ciba-Geigy under the trade name Tinopal SOP®. This brightener is almost insoluble in water, i.e. it has a solubility being lower than 1 gram per liter. Another example of such a brightener is bis(sulfobenzofuranyl)biphenyl, commercially available from Ciba-Geigy under the trade name Tinopal PLC®.

By "hydrophobic brighteners", it is to be understood herein any brightener whose solubility in water is lower than 10 grams per liter at 25° C. By "solubility" of a given compound, it is to be understood herein the amount of said compound solubilized in deionized water at 25° C. Thus, a compound having a solubility being lower than 10 grams per liter means that when less than 10 grams of said given compound is incorporated in deionized water at 25° C. said compound is entirely dissolved in said water, i.e. a clear and stable solution is obtained. In other words, incorporating 10 grams per liter or more of said given compound in water will result in a precipitation of said compound in said medium. Accordingly, by "hydrophilic brighteners", it is to be understood herein any brightener whose solubility in water is higher or equal to 10 grams per liter at 25° C.

Where present, brightener is incorporated at a level of from 0.001% to 1.0%, preferably from 0.005% to 0.5%, more preferably from 0.005% to 0.3% and most preferably from 0.008% to 0.1%, by weight of the composition.

Where hydrophobic brighteners are present in the compositions herein they may both be solubilized or suspended in the compositions of the present invention. Such brighteners solubilisation can be for example achieved by means of a surfactant or a mixture thereof as described herein after. Various surfactants may be used for this purpose like C8–C20 alkyl aryl sulphonates as described for example in U.S. Pat. No. 4,623,476 or amine oxides as described for example in EP-A-186386. Preferred surfactants also called "co-surfactants" to solubilise and/or suspend such a hydrophobic brightener are anionic surfactants including alkyl sulphates or alkylalkoxy sulphates having from 4 to 30 carbon atoms in the alkyl chain, or alkylethoxycarboxylates having from 6 to 30 carbon atoms in the alkyl chain such as Akyposoft® 100 NV from Chemy or Sandosan LNCS from Sandoz. Preferred are C12–C14 alkyethoxysulphates. Such co-surfactants herein should be used in amounts required to solubilize the hydrophobic brightener in need thereof.

Generally, when a co-surfactant is used, the liquid compositions of the present inventions are prepared in a process wherein the hydrophobic brightener and the co-surfactant are first mixed to form a premix, before the premix is then mixed with the remainder of the composition which has been separately prepared.

Alternatively, the hydrophobic brightener may be suspended by means of a specific suspending agent, like polymers and/or colloidal particulate silicate. Any polymers known to those skilled in the art as having suspending properties are suitable for use herein including those described for example in EP-A-206718.

Chelating Agents

Accordingly, the compositions of the present invention may comprise a chelating agent as a preferred optional ingredient. Suitable chelating agents may be any of those known to those skilled in the art such as the ones selected from the group comprising phosphonate chelating agents, amino carboxylate chelating agents, other carboxylate chelating agents, polyfunctionally-substituted aromatic chelating agents, ethylenediamine N,N'-disuccinic acids, or mixtures thereof.

A chelating agent may be desired in the compositions of the present invention as it may contribute to reduce tensile strength loss of fabrics and/or color damage, especially in a laundry pretreatment application. Indeed, the chelating agents inactivate the metal ions present on the surface of the fabrics and/or in the cleaning compositions (neat or diluted) that otherwise would contribute to the radical decomposition of the peroxygen bleach.

Suitable phosphonate chelating agents for use herein may include alkali metal ethane 1-hydroxy diphosphonates (HEDP), alkylene poly (alkylene phosphonate), as well as amino phosphonate compounds, including amino aminotri (methylene phosphonic acid) (ATMP), nitrilo trimethylene phosphonates (NTP), ethylene diamine tetra methylene phosphonates, and diethylene triamine penta methylene phosphonates (DTPMP). The phosphonate compounds may be present either in their acid form or as salts of different cations on some or all of their acid functionalities. Preferred phosphonate chelating agents to be used herein are diethylene triamine penta methylene phosphonate (DTPMP) and ethane 1-hydroxy diphosphonate (HEDP). Such phosphonate chelating agents are commercially available from Monsanto under the trade name DEQUEST®.

Polyfunctionally-substituted aromatic chelating agents may also be useful in the compositions herein. See U.S. Pat. No. 3,812,044, issued May 21, 1974, to Connor et al. Preferred compounds of this type in acid form are dihydroxydisulfobenzenes such as 1,2-dihydroxy-3,5-disulfobenzene.

A preferred biodegradable chelating agent for use herein is ethylene diamine N,N'-disuccinic acid, or alkali metal, or alkaline earth, ammonium or substitutes ammonium salts thereof or mixtures thereof. Ethylenediamine N,N'-disuccinic acids, especially the (S,S) isomer have been extensively described in U.S. Pat. No. 4,704,233, Nov. 3, 1987, to Hartman and Perkins. Ethylenediamine N,N'-disuccinic acids is, for instance, commercially available under the tradename ssEDDS® from Palmer Research Laboratories.

Suitable amino carboxylates for use herein include ethylene diamine tetra acetates, diethylene triamine pentaacetates, diethylene triamine pentaacetate (DTPA),N-hydroxyethylethylenediamine triacetates, nitrilotri-acetates, ethylenediamine tetrapropionates, triethylenetetraaminehexa-acetates, ethanol-diglycines, propylene diamine tetracetic acid (PDTA) and methyl glycine di-acetic acid (MGDA), both in their acid form, or in their alkali metal, ammonium, and substituted ammonium salt forms. Particularly suitable amino carboxylates to be used herein are diethylene triamine penta acetic acid, propylene diamine tetracetic acid (PDTA) which is, for instance, commercially available from BASF under the trade name Trilon FS® and methyl glycine di-acetic acid (MGDA).

Further carboxylate chelating agents for use herein include salicylic acid, aspartic acid, glutamic acid, glycine, malonic acid or mixtures thereof.

Another chelating agent for use herein is of the formula:

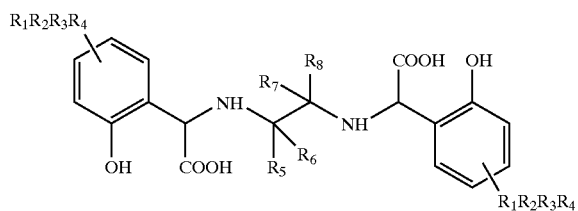

wherein $R_1$, $R_2$, $R_3$, and $R_4$ are independently selected from the group consisting of —H, alkyl, alkoxy, aryl, aryloxy, —Cl, —Br, —NO$_2$, —C(O)R', and —SO$_2$R''; wherein R' is selected from the group consisting of —H, —OH, alkyl, alkoxy, aryl, and aryloxy; R'' is selected from the group consisting of alkyl, alkoxy, aryl, and aryloxy; and $R_5$, $R_6$, $R_7$, and $R_8$ are independently selected from the group consisting of —H and alkyl.

Particularly preferred chelating agents for use herein are amino aminotri(methylene phosphonic acid), di-ethylene-triamino-pentaacetic acid, diethylene triamine penta methylene phosphonate, 1-hydroxy ethane diphosphonate, ethylenediamine N,N'-disuccinic acid, and mixtures thereof.

Typically, the compositions according to the present invention may comprise up to 5% by weight of the total composition of a chelating agent, or a mixture thereof, preferably from 0.01% to 1.5% by weight and more preferably from 0.01% to 0.5%.

Hydrotrope

Another preferred component of the present invention is a hydrotrope. Any suitable hydrotrope known in the art can be used herein. Preferred hydrotropes include the sulphonated hydrotropes, for example the alkyl aryl sulphonates or alkyl aryl sulphonic acids.

Preferred hydrotropes are selected from xylene, toluene, cumene, naphthalene sulphonate or sulphonic acid and mixtures thereof. Couterions being preferably selected from sodium, potassium, calcium and ammonium.

Typically, the compositions may preferably comprise from 0.01% to 20% by weight of a hydrotrope, more preferably from 0.05% to 10% and most preferably from 0.1% to 5%.

Radical Scavengers

The compositions of the present invention may if necessary include a further radical scavenger. Suitable further radical scavengers for use herein include the well-known substituted mono and dihydroxy benzenes and their analogs, alkyl and aryl carboxylates and mixtures thereof. Preferred such further radical scavengers for use herein include di-tert-butyl hydroxy toluene (BHT), hydroquinone, di-tert-butyl hydroquinone, mono-tert-butyl hydroquinone, tert-butyl-hydroxy anysole, benzoic acid, toluic acid, catechol, t-butyl catechol, benzylamine, 1,1,3-tris(2-methyl-4-hydroxy-5-t-butylphenyl) butane, n-propyl-gallate or mixtures thereof and highly preferred is di-tert-butyl hydroxy toluene. Such radical scavengers like N-propyl-gallate may be commercially available from Nipa Laboratories under the trade name Nipanox S1®. Radical scavengers when used, are typically present herein in amounts ranging from up to 10% by weight of the total composition, preferably from 0.001% to 2% and more preferably from 0.001% to 0.5% by weight.

The presence of further radical scavengers may further contribute to reduce tensile strength loss of fabrics and/or color damage when the compositions of the present invention are used in any laundry application, especially in a laundry pretreatment application.

Antioxidants

The compositions according to the present invention may further comprise an antioxidant or mixtures thereof.

Typically, the compositions herein may comprise up to 10% by weight of the total composition of an antioxidant or mixtures thereof, preferably from 0.002% to 5%, more preferably from 0.005% to 2%, and most preferably from 0.01% to 1%.

Suitable antioxidants for use herein include organic acids like ascorbic acid, adipic acid and sorbic acid, or amines like lecithin, or aminoacids like glutamine, methionine and cysteine, or esters like ascorbil palmitate, ascorbil stearate and triethylcitrate, or mixtures thereof. Preferred antioxidants for use herein are ascorbic acid, ascorbic palmitate, lecithin or mixtures thereof.

Bleach Activators

As an optional ingredient, the compositions of the present invention may comprise a bleach activator or mixtures thereof. By "bleach activator", it is meant herein a compound which reacts with hydrogen peroxide to form a peracid. The peracid thus formed constitutes the activated bleach. Suitable bleach activators to be used herein include those belonging to the class of esters, amides, imides, or anhydrides. Examples of suitable compounds of this type are disclosed in British Patent GB 1 586 769 and GB 2 143 231 and a method for their formation into a prilled form is described in European Published Patent Application EP-A-62 523. Suitable examples of such compounds to be used herein are tetracetyl ethylene diamine (TAED), sodium 3,5,5 trimethyl hexanoyloxybenzene sulphonate, diperoxy dodecanoic acid as described for instance in U.S. Pat. No. 4,818,425 and nonylamide of peroxyadipic acid as described for instance in U.S. Pat. No. 4,259,201 and n-nonanoyloxybenzenesulphonate (NOBS). Also suitable are N-acyl caprolactams selected from the group consisting of substituted or unsubstituted benzoyl caprolactam, octanoyl caprolactam, nonanoyl caprolactam, hexanoyl caprolactam, decanoyl caprolactam, undecenoyl caprolactam, formyl caprolactam, acetyl caprolactam, propanoyl caprolactam, butanoyl caprolactam pentanoyl caprolactam or mixtures thereof. A particular family of bleach activators of interest was disclosed in EP 624 154, and particularly preferred in that family is acetyl triethyl citrate (ATC). Acetyl triethyl citrate has the advantage that it is environmental-friendly as it eventually degrades into citric acid and alcohol. Furthermore, acetyl triethyl citrate has a good hydrolytical stability in the product upon storage and it is an efficient bleach activator. Finally, it provides good building capacity to the composition. The compositions according to the present invention may comprise from 0.01% to 20% by weight of the total composition of said bleach activator, or mixtures thereof, preferably from 1% to 10%, and more preferably from 3% to 7%

Foam Reducing System

The compositions according to the present invention may comprise a foam reducing agent or a mixture thereof. Any foam reducing agents known to those skilled in the art are suitable for use herein. In a preferred embodiment a foam system comprising a fatty acid together with a capped alkoxylated nonionic surfactant as defined herein after and/or silicone is used.

Typically, the compositions herein may comprise from % to 10% by weight of the total composition of a fatty acid or a mixture thereof, preferably from % to 5% and more preferably from % to 5%.

Typically, the compositions herein may comprise from % to 20% by weight of the total composition of a capped alkoxylated nonionic surfactant as defined herein or a mixture thereof, preferably from % to 10% and more preferably from % to 5%.

Typically, the compositions herein may comprise from % to 5% by weight of the total composition of a silicone or a mixture thereof, preferably from % to 1% and more preferably from % to 0.5%.

Suitable fatty acids for use herein are the alkali salts of a $C_8$–$C_{24}$ fatty acid. Such alkali salts include the metal fully saturated salts like sodium, potassium and/or lithium salts as well as the ammonium and/or alkylammonium salts of fatty acids, preferably the sodium salt. Preferred fatty acids for use herein contain from 8 to 22 carbon atoms, preferably from 8 to 20 and more preferably from 8 to 18.

Suitable fatty acids may be selected from caprylic acid, capric acid, lauric acid, myristic acid, palmitic acid, stearic acid and mixtures of fatty acids suitably hardened, derived from natural sources such as plant or animal esters (e.g., palm oil, coconut oil, soybean oil, castor oil, tallow, ground oil, whale and fish oils and/or babassu oil.

For example Coconut Fatty Acid is commercially available from UNICHEMA under the name PRIFAC 5900®.

Suitable capped alkoxylated nonionic surfactants for use herein are according to the formula:

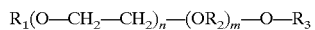

wherein $R_1$ is a $C_8$–$C_{24}$ linear or branched alkyl or alkenyl group, aryl group, alkaryl group, preferably $R_1$ is a $C_8$–$C_{18}$ alkyl or alkenyl group, more preferably a $C_{10}$–$C_{15}$ alkyl or alkenyl group, even more preferably a $C_{10}$–$C_{15}$ alkyl group;

wherein $R_2$ is a $C_1$–$C_{10}$ linear or branched alkyl group, preferably a $C_2$–$C_{10}$ linear or branched alkyl group, preferably a $C_3$ group;

wherein $R_3$ is a $C_1$–$C_{10}$ alkyl or alkenyl group, preferably a $C_1$–$C_5$ alkyl group, more preferably methyl;

and wherein n and m are integers independently ranging in the range of from 1 to 20, preferably from 1, to 10, more preferably from 1 to 5; or mixtures thereof.

These surfactants are commercially available from BASF under the trade name Plurafac®, from HOECHST under the trade name Genapol® or from ICI under the trade name Symperonic®. Preferred capped nonionic alkoxylated surfactants of the above formula are those commercially available under the tradename Genapol® L 2.5 NR from Hoechst, and Plurafac® from BASF.

Suitable silicones for use herein include any silicone and silica-silicone mixtures. Silicones can be generally represented by alkylated polysiloxane materials while silica is normally used in finely divided forms exemplified by silica aerogels and xerogels and hydrophobic silicas of various types. These materials can be incorporated as particulates in which the silicone is advantageously releasably incorporated in a water-soluble or water-dispersible, substantially non-surface-active detergent impermeable carrier. Alternatively, the silicone can be dissolved or dispersed in a liquid carrier and applied by spraying on to one or more of the other components.

Actually in industrial practice, the term "silicone" has become a generic term which encompasses a variety of relatively high-molecular-weight polymers containing siloxane units and hydrocarbyl groups of various types. Indeed, silicone compounds have been extensively described in the art, see for instance U.S. Pat. No. 4,076,648, U.S. Pat. No. 4,021,365, U.S. Pat. No. 4,749,740, U.S. Pat. No. 4,983,316, EP 150 872, EP 217 501 and EP 499 364. The silicone compounds disclosed therein are suitable in the context of the present invention. Generally, the silicone compounds can be described as siloxanes having the general structure:

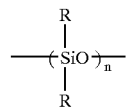

wherein n is from 20 to 2000, and where each R independently can be an alkyl or an aryl radical. Examples of such substituents are methyl, ethyl, propyl, isobutyl, and phenyl. Preferred polydiorganosiloxanes are polydimethylsiloxanes having trimethylsilyl end blocking units and having a viscosity at 25° C. of from $5\times10^{-5}$ $m^2$/s to 0.1 $m^2$/s, i.e. a value of n in the range 40 to 1500. These are preferred because of their ready availability and their relatively low cost.

A preferred type of silicone compounds useful in the compositions herein comprises a mixture of an alkylated siloxane of the type hereinabove disclosed and solid silica. The solid silica can be a fumed silica, a precipitated silica or a silica made by the gel formation technique. The silica particles can be rendered hydrophobic by treating them with diakylsilyl groups and/or trialkylsilane groups either bonded directly onto the silica or by means of silicone resin. A preferred silicone compound comprises a hydrophobic silanated, most preferably trimethylsilanated silica having a particle size in the range from 10 mm to 20 mm and a specific surface area above 50 $m^2$/g. Silicone compound s employed in the compositions according to the present invention suitably have an amount of silica in the range of 1 to 30% (more preferably 2.0 to 15%) by weight of the total weight of the silicone compounds resulting in silicone compounds having an average viscosity in the range of from $2\times10^{-4}$ $m^2$/s to 1 $m^2$/s. Preferred silicone compounds may have a viscosity in the range of from $5\times10^{-3}$ $m^2$/s to 0.1 $m^2$/s. Particularly suitable are silicone compounds with a viscosity of $2\times10^{-2}$ $m^2$/s or $4.5\times10^{-2}$ $m^2$/s.

Suitable silicone compounds for use herein are commercially available from various companies including Rhone Poulenc, Fueller and Dow Corning. Examples of silicone compounds for use herein are Silicone DB® 100 and Silicone Emulsion 2-3597® both commercially available from Dow Corning.

Another silicone compound is disclosed in Bartollota et al. U.S. Pat. No. 3,933,672. Other particularly useful silicone compounds are the self-emulsifying silicone compounds, described in German Patent Application DTOS 2 646 126 published Apr. 28, 1977. An example of such a compound is DC-544®, commercially available from Dow Corning, which is a siloxane-glycol copolymer.

Typically preferred silicone compounds are described in European Patent application EP-A-573699. Said compositions can comprise a silicone/silica mixture in combination with fumed nonporous silica such as Aerosil®.

Process of Cleaning Fabrics

In the present invention, the liquid cleaning composition of the present invention needs to be contacted with the fabrics to be bleached. This can be done either in a so-called "pretreatment mode", where the liquid composition is applied neat onto said fabrics before the fabrics are rinsed, or washed then rinsed, or in a "soaking mode" where the liquid composition is first diluted in an aqueous bath and the fabrics are immersed and soaked in the bath, before they are rinsed, or in a "through the wash mode", where the liquid composition is added on top of a wash liquor formed by dissolution or dispersion of a typical laundry detergent.

It is also essential in both cases, that the fabrics be rinsed after they have been contacted with said composition, before said composition has completely dried off.

In the pretreatment mode, the process comprises the steps of applying said liquid composition in its neat form onto said fabrics, or at least soiled portions thereof, and subsequently rinsing, or washing then rinsing said fabrics. In this mode, the neat compositions can optionally be left to act onto said fabrics for a period of time ranging from 1 min. to 1 hour, before the fabrics are rinsed, or washed then rinsed, provided that the composition is not left to dry onto said fabrics. For particularly though stains, it may be appropriate to further rub or brush said fabrics by means of a sponge or a brush, or by rubbing two pieces of fabrics against each other.

In another mode, generally referred to as "soaking", the process comprises the steps of diluting said liquid composition in its neat form in an aqueous bath so as to form a diluted composition. The dilution level of the liquid composition in an aqueous bath is typically up to 1:85, preferably up to 1:50 and more preferably about 1:25 (composition:water). The fabrics are then contacted with the aqueous bath comprising the liquid composition, and the fabrics are finally rinsed, or washed then rinsed. Preferably in that embodiment, the fabrics are immersed in the aqueous bath comprising the liquid composition, and also preferably, the fabrics are left to soak therein for a period of time ranging from 1 minute to 48 hours, preferably from 1 hour to 24 hours.

In yet another mode which can be considered as a sub-embodiment of "soaking", generally referred to as "bleaching through the wash", the liquid composition is used as a so-called laundry additive. And in that embodiment the aqueous bath is formed by dissolving or dispersing a conventional laundry detergent in water. The liquid composition in its neat form is contacted with the aqueous bath, and the fabrics are then contacted with the aqueous bath containing the liquid composition. Finally, the fabrics are rinsed.

Depending on the end-use envisioned, the compositions herein can be packaged in a variety of containers including conventional bottles, bottles equipped with roll-on, sponge, brush or sprayer.

Although preferred application of the compositions described herein is laundry application and especially laundry pretreatment, the compositions according to the present invention may also be used as a household cleaner in the cleaning of bathroom surfaces or kitchen surfaces.

Alternative Applications for Use of Radical Scavengers

Whilst the use of the free radical scavengers of the present invention in cleaning compositions is the currently preferred application, it is also envisages that the radical scavengers may equally be used in alternative applications. Such alternative applications include diagnosis, treatment of allergic reactions, and treatment of ageing, including brain ageing and other neurodegenerative diseases and ageing of foods and fuels.

EXAMPLES

The invention is further illustrated by the following beaching composition examples. All levels are presented as percentage by weight of the composition.

|  | Formulation (w/w %) | | | | | |
| --- | --- | --- | --- | --- | --- | --- |
|  | A | B | C | D | E | F |
| H$_2$O$_2$ bleach | 7 | 7 | 4 | 4 | — | — |
| Hypochlorite bleach | — | — | — | — | 5 | 3 |
| BLEACH ACTIVATOR 3 | — | — | 1 | 3 | — | — |
| Surfactant: |  |  |  |  |  |  |
| Nonionic | 3 | 4 | 10 | 12 | — | — |
| Anionic | 2 | — | 6 | 12 | — | 5 |
| Zwitterionic | — | 2 | — | — | — | 1 |
| BUFFER | — | 0.5 | 1 | — | 1.5 | 1.5 |
| CHELANT | 0.1 | 0.1 | 0.1 | 0.5 | — | 0.1 |
| SCAVENGER | 0.1 | 0.07 | 0.01 | 0.5 | 0.1 | 0.5 |
| PERFUME | 0.15 | 0.20 | 0.2 | 0.5 | — | 0.2 |
| MINORS AND WATER to balance |  |  |  |  |  |  |

What is claimed is:

1. A method of scavenging free radicals comprising adding a chromophoric compound having the following formula:

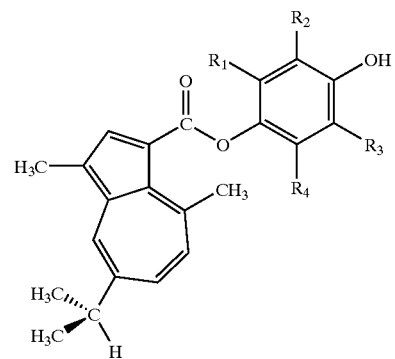

wherein the R$_1$–R$_4$ groups can be either hydrogen, methyl, or any alkyl, alkenyl or alkynyl group having from 1 to 20 carbons atoms, to a material in need of free radical scavenging.

2. A method according to claim 1 wherein the R$_1$–R$_4$ groups of said chromophoric compound are selected from the group consisting of hydrogen, an alkyl group having from 1 to 3 carbon atoms and mixtures thereof.

3. A food or fuel composition comprising a chromophoric compound having the following formula:

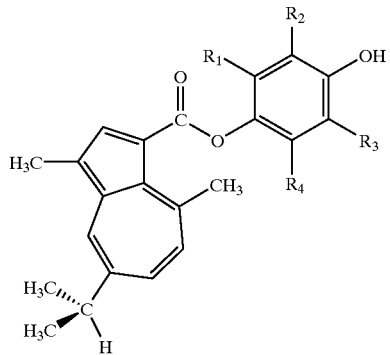

wherein the $R_1$–$R_4$ groups can be either hydrogen, methyl, or any alkyl, alkenyl or alkynyl group having from 1 to 20 carbons atoms, to a material in need of free radical scavenging and a food or fuel.

4. A food or fuel preservative according to claim 3 wherein the $R_1$–$R_4$ groups of said chromophoric compound are selected from the group consisting of hydrogen, an alkyl group having from 1 to 3 carbon atoms and mixtures thereof.

5. A method of preserving a food or fuel comprising adding a chromophoric compound having the following formula:

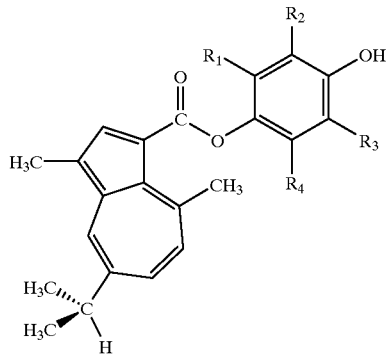

wherein the $R_1$–$R_4$ groups can be either hydrogen, methyl, or any alkyl, alkenyl or alkynyl group having from 1 to 20 carbons atoms, to a material in need of free radical scavenging.

6. A method according to claim 5 wherein the $R_1$–$R_4$ groups of said chromophoric compound are selected from the group consisting of hydrogen, an alkyl group having from 1 to 3 carbon atoms and mixtures thereof.

7. A medicinal composition comprising a chromophoric compound having the following formula:

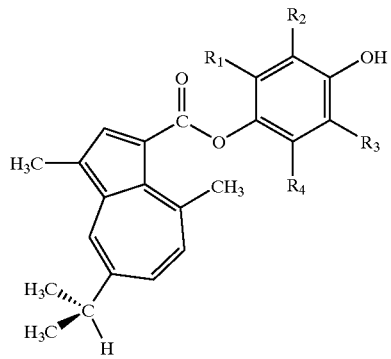

wherein the $R_1$–$R_4$ groups can be either hydrogen, methyl, or any alkyl, alkenyl or alkynyl group having from 1 to 20 carbons atoms, to a material in need of free radical scavenging and a medicine.

8. A medicinal composition according to claim 7 wherein the $R_1$–$R_4$ groups of said chromophoric compound are selected from the group consisting of hydrogen, an alkyl group having from 1 to 3 carbon atoms and mixtures thereof.

9. A process of identifying the presence of a free radical in a bleaching composition comprising the steps of:
   a.) mixing a bleaching agent and a chromophoric compound having the following formula:

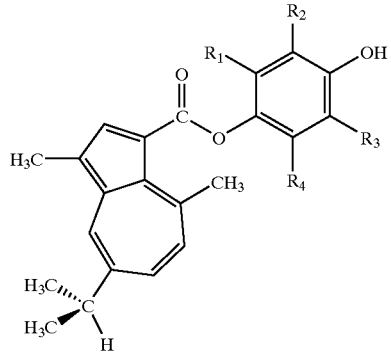

wherein the $R_1$–$R_4$ groups can be either hydrogen, methyl, or any alkyl, alkenyl or alkynyl group having from 1 to 20 carbons atoms, to a material in need of free radical scavenging; and
   b.) measuring the intensity of the colour change of said compound.

10. A process according to claim 9 wherein the $R_1$–$R_4$ groups of said chromophoric compound are selected from the group consisting of hydrogen, an alkyl group having from 1 to 3 carbon atoms and mixtures thereof.

* * * * *